United States Patent
Hendriks et al.

(10) Patent No.: US 9,955,927 B2
(45) Date of Patent: May 1, 2018

(54) SYSTEM FOR DETECTING GLOBAL PATIENT MOVEMENT DURING IMAGING PROCEDURES

(75) Inventors: Bernardus Hendrikus Wilhelmus Hendriks, Eindhoven (NL); Michael Cornelis Van Beek, Eindhoven (NL); Peter-Andre Redert, Eindhoven (NL); Frederik Jan De Bruijn, Eindhoven (NL); Drazenko Babic, Eindhoven (NL); Robert Johannes Frederik Homan, Eindhoven (NL); Ralph Braspenning, Eindhoven (NL); Wei Pien Lee, Eindhoven (NL); Karl Catharina Van Bree, Eindhoven (NL); Caifeng Shan, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 78 days.

(21) Appl. No.: 13/320,358

(22) PCT Filed: May 10, 2010

(86) PCT No.: PCT/IB2010/052042
§ 371 (c)(1),
(2), (4) Date: Nov. 14, 2011

(87) PCT Pub. No.: WO2010/131180
PCT Pub. Date: Nov. 18, 2010

(65) Prior Publication Data
US 2012/0170824 A1     Jul. 5, 2012

(30) Foreign Application Priority Data

May 13, 2009 (EP) .................................. 09160106

(51) Int. Cl.
*G06K 9/00* (2006.01)
*A61B 6/02* (2006.01)
(Continued)

(52) U.S. Cl.
CPC ............ *A61B 6/025* (2013.01); *A61B 6/4423* (2013.01); *A61B 6/4441* (2013.01);
(Continued)

(58) Field of Classification Search
None
See application file for complete search history.

(56) References Cited

U.S. PATENT DOCUMENTS 5,727,554 A    3/1998 Kalend et al.
5,769,789 A *  6/1998 Wang ................. G01R 33/28
                                                     382/131

(Continued)

FOREIGN PATENT DOCUMENTS

JP    2008043567 A    2/2008
WO    2004089204 A1   10/2004
(Continued)

OTHER PUBLICATIONS

Wiesner, Stefan, and Ziv Yaniv. "Monitoring patient respiration using a single optical camera." Engineering in Medicine and Biology Society, 2007. EMBS 2007. 29th Annual International Conference of the IEEE. IEEE, 2007.*

(Continued)

*Primary Examiner* — Nirav G Patel

(57) ABSTRACT

A system for accurately detecting a patient's movement during imaging procedures includes a camera for providing a stream of camera images of a part of a patient's exterior and a fiducial element mountable on part of the patient's exterior. The fiducial element is detectable in the stream of images. An image processor is configured to detect a dis- (Continued)

placement of the fiducial element based on consecutive images including in at least the stream of images and to generate an output signal indicative of the displacement. The fiducial element has an in-plane stiffness which is substantially larger than an in-plane stiffness of the part of the patient's exterior. In addition, the fiducial element and the part of the patient's exterior are provided with substantially equal outer in-plane dimensions.

17 Claims, 4 Drawing Sheets

(51) Int. Cl.
    *A61B 6/00*     (2006.01)
    *A61B 90/00*     (2016.01)

(52) U.S. Cl.
    CPC .......... *A61B 6/5247* (2013.01); *A61B 90/361* (2016.02); *A61B 90/39* (2016.02); *A61B 2090/376* (2016.02)

(56) References Cited

U.S. PATENT DOCUMENTS

| | | | |
|---|---|---|---|
| 6,435,717 | B1 | 9/2002 | Kohler et al. |
| 6,741,883 | B2 | 5/2004 | Gildenberg et al. |
| 6,928,142 | B2 | 8/2005 | Shao et al. |
| 7,125,165 | B2 | 10/2006 | Lutjens et al. |
| 8,160,675 | B2 | 4/2012 | Jaffray et al. |
| 2002/0012420 | A1* | 1/2002 | Bani-Hashemi et al. ...... 378/63 |
| 2002/0188194 | A1* | 12/2002 | Cosman ................... 600/426 |
| 2004/0116804 | A1* | 6/2004 | Mostafavi ............. A61B 5/113 600/428 |
| 2004/0247074 | A1 | 12/2004 | Langton |
| 2004/0247076 | A1* | 12/2004 | Navab et al. .................. 378/63 |
| 2008/0287807 | A1 | 11/2008 | Chase et al. |
| 2009/0116719 | A1* | 5/2009 | Jaffray et al. ................ 382/131 |
| 2009/0141958 | A1* | 6/2009 | Graumann et al. .......... 382/132 |
| 2010/0063387 | A1 | 3/2010 | Timinger |

FOREIGN PATENT DOCUMENTS

| | | |
|---|---|---|
| WO | 2007035907 A2 | 3/2007 |
| WO | 2007073988 A1 | 7/2007 |
| WO | 2007136967 A2 | 11/2007 |
| WO | 2010067281 A1 | 6/2010 |

OTHER PUBLICATIONS

"Overview of materials for Low Density Polyethylene (LDPE), Molded." Online Materials Information Resource—MatWeb. N.p., Jan. 1, 2011. Web. May 1, 2017.*

By B. Gao et al. "Investigation of Soft Tissue Movement During Level Walking: Translations and Rotations of Skin Markers" Biomechanics, 41 (15) Nov. 14, 2008. pp. 3189-3195.

By H. Yan et al. Investigation of the Location Effect of External Markers in Respiratory-Gated Radiotherapy Appl. Clinical Med. Phy., 9 (2), Published 2008. pp. 57-68.

Schweikard, A. et al., "Respiration tracking in radiosurgery", Oct. 31, 2004, vol. 31, No. 10, p. 2738-2741.

Meeks, S.L. et al., "Optically guided patient positioning techniques", Seminars in Radiation Oncology, Jul. 1, 2005, PA, vol. 15, Nr. 3, Abstract.

Bader, D.L. et al., "Mechanical characteristics of skin and underlying tissues in vivo", Biomaterials, Oct. 1, 1983, vol. 4, Nr. 4, pp. 305=308.

* cited by examiner

SYSTEM FOR DETECTING GLOBAL PATIENT MOVEMENT DURING IMAGING PROCEDURES

FIELD OF THE INVENTION

The invention relates to a system for detecting a patient's movement during imaging procedures.

BACKGROUND OF THE INVENTION

US-A 2008/0287807 A1 discloses a method for breast cancer screening. For the purpose of tumor detection, digital imaging of an actuated breast is employed to determine tissue surface motion. On the basis of said tissue surface motion, an internal stiffness distribution is reconstructed, whereby regions of high stiffness suggest cancer. The method according to US-A 2008/0287807 A1 comprises a step of placing a plurality of fiducial element markers on a tissue surface, a step of actuating the tissue surface, a step of imaging the tissue surface with an array of digital cameras, a step of choosing motion invariant properties of the fiducial element markers, a step of tracking the fiducial element markers from image to image and a step of using the tracked motion in each camera and the camera calibration to measure tissue surface motion.

During imaging procedures performed by e.g. Magnetic Resonance Imaging (MRI) or X ray devices, it is essential for the medical professional to be provided with accurate information regarding global movements of the patient's exterior. The method disclosed in US-A 2008/0287807 A1 is typically arranged for detecting local movements of the patient's exterior, but is not capable of detecting global movement of the patient's exterior.

SUMMARY OF THE INVENTION

It is an object of the invention to provide a system of the kind defined in the opening paragraph capable of accurately detecting a global movement of a patient's exterior during imaging procedures. This object is achieved by the system according to the invention. The system according to the invention comprises a camera for providing a stream of camera images of a part of a patient's exterior, a fiducial element mountable on said part of the patient's exterior, wherein the fiducial element is detectable in the stream of camera images, wherein the fiducial element has an in-plane stiffness substantially larger than an in-plane stiffness of said part of the patient's exterior, and wherein the fiducial element and said part of the patient's exterior are provided with substantially equal outer in-plane dimensions, and an image processor for detecting a displacement of the fiducial element based on consecutive camera images comprised in the stream of camera images, and for generating an output signal indicative for said displacement.

Through providing the fiducial element with a large in-plane stiffness compared to the in-plane-stiffness of the part of the patient's exterior, and by providing the fiducial and the part of the patient's exterior with substantially equal outer in-plane dimensions, local movements of the patient's exterior, i.e. the patients skin, relative to a patient's skeleton along a direction parallel to the fiducial element's plane are effectively prevented from, as will be explained hereinafter. As a result, presuming the patient maintains a stationary position, the patient's exterior is limited to move along a direction perpendicular to the fiducial, which is a global movement. The latter global movement is made observable via the fiducial element. By making the fiducial element detectable in a stream of camera images, the system according to the invention effectively increases the accuracy of detecting global movement of the patient's exterior.

In addition, the system according to the invention enables detecting global movement of the patient's exterior in a painless and efficient way. Namely, the system according to the invention effectively circumvents rigidly attaching fiducial elements to the patient's skeleton for the purpose of accurately detecting global movement of the patient's exterior, which would be an invasive procedure requiring additional preparation of the patient, making it time consuming and costly. Further, the system according to the invention effectively circumvents the application of a significant large number of relatively small fiducial elements attached to the patient's exterior, whereby local movements are compensated for by leaving out of consideration mutual displacements of said relatively small fiducials, which is a rather difficult procedure subject to inaccuracies. That is, rather than counterbalancing local movements afterwards, the system according to the invention prevents the origination of local movements beforehand.

The fiducial element is typically manufactured from an adhesive and an additional layer mounted on the adhesive. The additional layer is preferably a metal, and more preferably aluminum.

In this document, a stream of camera images implies at least two camera images, but usually a plurality of camera images. It is stressed that in this document, a camera not necessarily implies an optical camera; the camera is responsive to a wavelength, which wavelength may be either in the visible spectrum, the infrared spectrum or the ultraviolet spectrum.

In this document, outer in-plane dimensions are considered dimensions defining a contour of said plane.

In this document, stiffness is defined as a resistance of a deformable body to deformation through an applied force or an applied torque. An in-plane stiffness means a stiffness along any imaginary axis comprised in the plane, hence in-plane stiffness does not include stiffness along any other imaginary axis having a component perpendicular to the plane. In this document, the fiducial element's in-plane stiffness is considered to be substantially larger than the in-plane stiffness associated with said part of the patient's exterior, in case the ratio of the fiducial element's in-plane stiffness to the in-plane stiffness of said part of the patient's exterior exceeds 10 to 1. Preferably, the aforementioned ratio exceeds 50 to 1, and more preferably, the latter ratio exceeds 100 to 1. Namely, by increasing the latter ratio, local movements of the patient's exterior along a direction parallel to the fiducial element's plane will be further decreased. Consequently, the accuracy of determining the patient's exterior global movements will be additionally increased. It is stressed that unlimitedly increasing said ratio is not a feasible option. Namely, it would result in a fiducial element having an in-plane stiffness such large compared to the patient's exterior, that the fiducial element would be barely mountable on the patient's exterior. Herein, mounting the fiducial element on the patient's exterior implies placing said fiducial element on the patient's exterior, and subsequently securing said fiducial element to the patient's exterior. It is furthermore noted that the in-plane stiffness associated with the part of the patient's exterior that is under examination, is mainly determined by its Young's modulus of elasticity, which modulus is dependent on the patient at hand, the body part at which the part of the patient's exterior is located, the patient's gender and parameters such as temperature and relative humidity. It is to be noted that in e.g. D. L. Bader and P. Bowker, *"Mechanical characteristics of skin and underlying tissues in vivo"*, Biomaterials, 4:305-308, 1983, a range of Young's moduli is presented for a human's exterior. For instance, the Young's modulus of a male patient's exterior at the forearm, amounts $1.51*10^{-3}$ [MPa] in case of indentation. Employing an equal way of loading, a female patient's exterior at the forearm is determined to amount $1.09*10^{-3}$ [MPa].

In this document, the in-plane dimensions of the fiducial element are in any case considered to be substantially equal to the in-plane dimensions of said part of the patient's exterior, if the fiducial element's outer in-plane dimensions at least exceed 1 cm by 1 cm. Preferably, the fiducial element's outer in-plane dimensions exceed 5 cm by 5 cm, and more preferably, the fiducial element's outer in-plane dimensions exceed 10 cm by 10 cm, provided that the fiducial element's outer in-plane dimensions remain substantially equal to the further outer in-plane dimensions of said part of the patient's exterior. Herein, the outer in-plane dimensions of the fiducial element are considered to be substantially equal to the further outer in-plane dimensions of the part of the patient's exterior in case the fiducial element's outer in-plane dimensions amount to 75% up to and including 125% of said further outer in-plane dimensions. Through increasing the fiducial element's in-plane dimensions, local movements of the patient's exterior along a direction parallel to the fiducial element's plane will be further decreased. Consequently, the accuracy of determining the patient's exterior global movements will be additionally increased. Furthermore, increasing the fiducial element's in-plane dimensions will improve a visibility of said fiducial element in the camera images.

In a preferred embodiment of the system according to the invention, the fiducial element has a buckling stiffness which is substantially larger than a buckling stiffness of the part of the patient's exterior. In this document, buckling is interpreted to be a deformation mode under a compressive mechanical stress, which deformation mode is characterized by exhibiting displacements along orientations different a direction in which the compressive mechanical stress is applied. It is to be noted that a buckling fiducial element manifests a deformation pattern perpendicular to the plane of the fiducial element, however, this deformation pattern is induced by a local deformation of the patient's exterior, and is therefore to be suppressed by the fiducial element. In this document, the fiducial element's buckling stiffness is considered to be substantially larger than the buckling stiffness associated with said part of the patient's exterior, in case the ratio of the fiducial element's buckling stiffness to the buckling stiffness of said part of the patient's exterior exceeds 10 to 1. Preferably, the aforementioned ratio exceeds 50 to 1, and more preferably, the latter ratio exceeds 100 to 1. Namely, by increasing the latter ratio, local movements of the patient's exterior will be decreased to a further extent by the fiducial element. Consequently, the accuracy of determining the patient's exterior global movements will be additionally increased. It is stressed that unlimitedly increasing the latter ratio is not a feasible option. Namely, it would result in a fiducial element having a buckling stiffness such large compared to the patient's exterior, that the fiducial element would be barely mountable on the patient's exterior. For the purpose of providing substantial buckling stiffness, the aforementioned additional layer has a thickness ranging from 50 μm to 500 μm, a.o. depending on the material employed to manufacture the additional layer.

In a further preferred embodiment of the system according to the invention, the system comprises a plurality of fiducial elements, wherein the fiducial elements are installable in mutually substantially non-parallel planes. This embodiment is advantageous in that it increases the accuracy with which global movement of the patient's exterior is detectable. Namely, by installing a plurality of fiducial elements in mutually substantially non-parallel planes, information regarding multiple directions along which the global movement of the patient's exterior may evolve will be obtained.

In a further preferred embodiment of the system according to the invention, the system comprises a further camera for providing a stream of further camera images of said part of the patient's exterior, wherein the camera and the further camera are being mutually rigidly supported for establishing a mutually predetermined spatial relationship, and wherein the fiducial element is detectable in the further camera image. The system furthermore comprises a data processor for rendering the stream of camera images and the stream of further camera images into a stream of composite camera images on the basis of a further spatial correlation between the stream of camera images and the stream of further camera images, which further spatial correlation is established by each fiducial element. Given a distance between optical axes associated with the camera and the further camera, a parallax is introduced. Consequently, three-dimensional information regarding the patient's exterior is obtained. As a result this embodiment advantageously increases an accuracy of detecting the global movement of the patient's exterior.

In a further preferred embodiment of the system according to the invention, the system comprises an X ray device for generating an X ray image of said part of a patient's interior, wherein at least the camera is supported by the X ray device for establishing a predetermined spatial relationship between the stream of camera images and the X ray image, and wherein the fiducial element is detectable in the X ray image. The system furthermore comprises a further data processor for updating the X ray image on the basis of the output signal generated by the image processor, and on the basis of a spatial correlation between at least the stream of camera images and the X ray image, which spatial correlation is established by the fiducial element. Preferably, provided the further camera is present, the further camera is supported by the X ray device as well. The spatial correlation between the stream of camera images and the X ray image, i.e. a correlating of the stream of camera images and the X ray image in spatial respect, is a onetime spatially correlating. Namely, since a predetermined spatial relationship between the camera and the X ray device is acquired through supporting the camera by the X ray device, the spatial correlation established through the fiducial, which fiducial is detectable in both the stream of camera images and the X ray image, is applicable for an indefinite time span thereafter. This embodiment has the advantage that it guarantees the X ray image to be consistent with an actual position and orientation of the patient's exterior, while exposing the patient to a minimum amount of potentially harmful X rays. Namely, the X ray image is allowed to be a onetime X ray image indeed through spatially correlating the stream of camera images and the X ray image and by subsequently updating the X ray image in conformance with a global movement of the patient's exterior on the basis of the output signal generated by the image processor. Nonetheless, the data processor may be configured for rendering a stream of X ray images and the stream of camera images into a stream of composite images. Herein, a camera refresh rate need not necessarily equal an X ray image refresh rate.

In a further preferred embodiment of the system according to the invention, the data processor is arranged for rendering the X ray image and at least the stream of camera images into a stream of composite images on the basis of said spatial correlation between the stream of camera images and the X ray image. This embodiment has the advantage that it enables a medical professional's ability to efficiently and precisely perform an image based medical intervention. Namely, this embodiment provides said medical professional with an image comprising information of both the patient's interior and exterior in a simultaneous way. Preferably, the data processor is arranged for rendering the X ray image and a stream of composite camera images into a stream of composite images.

In a preferred embodiment of the system according to the invention, the X ray device comprises a movable geometry, wherein at least the camera is being supported by said movable geometry. This embodiment has the advantage that the medical professional is permitted to freely choose a patient's location or orientation with regard to the camera, since a position or a viewing angle of the camera allows for adjustment, without cancelling the predetermined spatial relationship between the stream of camera images and the X ray image. This feature is of large assistance in generating the stream of camera images. Preferably, the movable geometry is embodied by a movable C arm which is usually present in nowadays X ray devices. In that way, the system according to the invention advantageously allows for seamless integration with a medical professional's convenient way of working. Furthermore, the movable C arm has the advantage of providing an entire rotational degree of freedom for the camera with respect to the surgical area. In addition, the movable C arm has the advantage that it enables a three dimensional reconstruction for the X ray image.

In a further preferred embodiment of the system according to the invention, the system comprises an instrument for performing a medical intervention, wherein the instrument is detectable in the stream of camera images and in the X ray image. This embodiment advantageously enables image guided surgery in a convenient and effective way. Namely, a geometry of the medical instrument is deducible by generating the X ray image of both the patient and the medical instrument. As a consequence, no elaborate programming of the instrument's geometry is required. Since the medical instrument is detectable in the stream of camera images, information regarding an instrument's location and orientation, can be updated in the stream of composite images on the basis of the spatial correlation between the X ray image and the stream of camera images. Hence, the medical professional is provided with information regarding the instrument's location and orientation, with respect to the patient's interior and exterior, by way of the stream of composite images. Preferably, the instrument comprises pulsed Light Emitting Diodes (LEDs) for enhancing its detectability in the stream of camera images hence in the stream of composite images.

In a further preferred embodiment of the system according to the invention, the camera is arranged for providing a beam of electromagnetic radiation for excitation of a contrast agent supplied to the patient. As a result, the stream of camera images is advantageously provided with a fluorescence characteristic, which fluorescence characteristic provides information regarding a patient's circulatory system. The latter information will preferably be available real time in the in the stream of camera images, hence the medical professional is provided with real time information regarding e.g. the patient's blood circulatory and lymphatic systems for e.g. detecting tumors. The contrast agent for example comprises dyes in small molecule form, which dyes remain in a patient's blood flow for a limited amount of time, typically a few minutes.

In a further preferred embodiment of the system according to the invention, the system comprises an illumination device arranged for projecting information comprised in the X ray image onto said part of the patient's exterior on the basis of the spatial correlation between the stream of camera images and the X ray image. This embodiment advantageously enables the medical professional to perform the image guided medical intervention even more safely and effectively. Namely, this embodiment effectively circumvents the need for translating the stream of composite images to said part of the patient's exterior through providing information regarding the patient's interior at the patient's exterior. Preferably, a projection of information comprised in the X ray image is compensated for a possible curvature of the patient's exterior on the basis of the stream of camera images.

In a further preferred embodiment of the system according to the invention, the illumination device is supported by the X ray device for establishing a further predetermined spatial relationship between the illumination device and the X ray device. This embodiment has the advantage that a projection of information comprised in the X ray image is easily performed, that is, without further spatial correlating. Since the camera is supported by the X ray device as well, a determined spatial relationship between the camera and the illumination device is obtained. Because the camera image has been spatially correlated to the X ray image, information comprised in the X ray image is projected to the patient's exterior without further calibration of the illumination device.

In a further preferred embodiment of the system according to the invention, the illumination device is arranged for radiation sterilization. For this purpose the illumination device is arranged to transmit a beam of electromagnetic radiation, which electromagnetic radiation has a wavelength at which the electromagnetic radiation is absorbable by the DNA of infectious agents such as bacteria and other pathogenic cells. For instance, UV radiation at a wavelength of about 250 [nm] is employed. This embodiment has the advantage of being capable to sterilize an environment of the system according to the invention, e.g. a surgical table, more effectively. Namely, compared to sterilization based on solvents, the chance of successful sterilization is significantly larger. An additional advantage of this embodiment is in the fact that the sterilization is quickly and easily performed, that is, without interference of other systems. Preferably the illumination device is attached to a movable C arm presumably comprised in the X ray device. In that case, the sterilization is performed by making a rotation, preferably a full rotation, employing the movable C arm geometry.

DETAILED DESCRIPTION OF THE EMBODIMENTS

Figure 1:
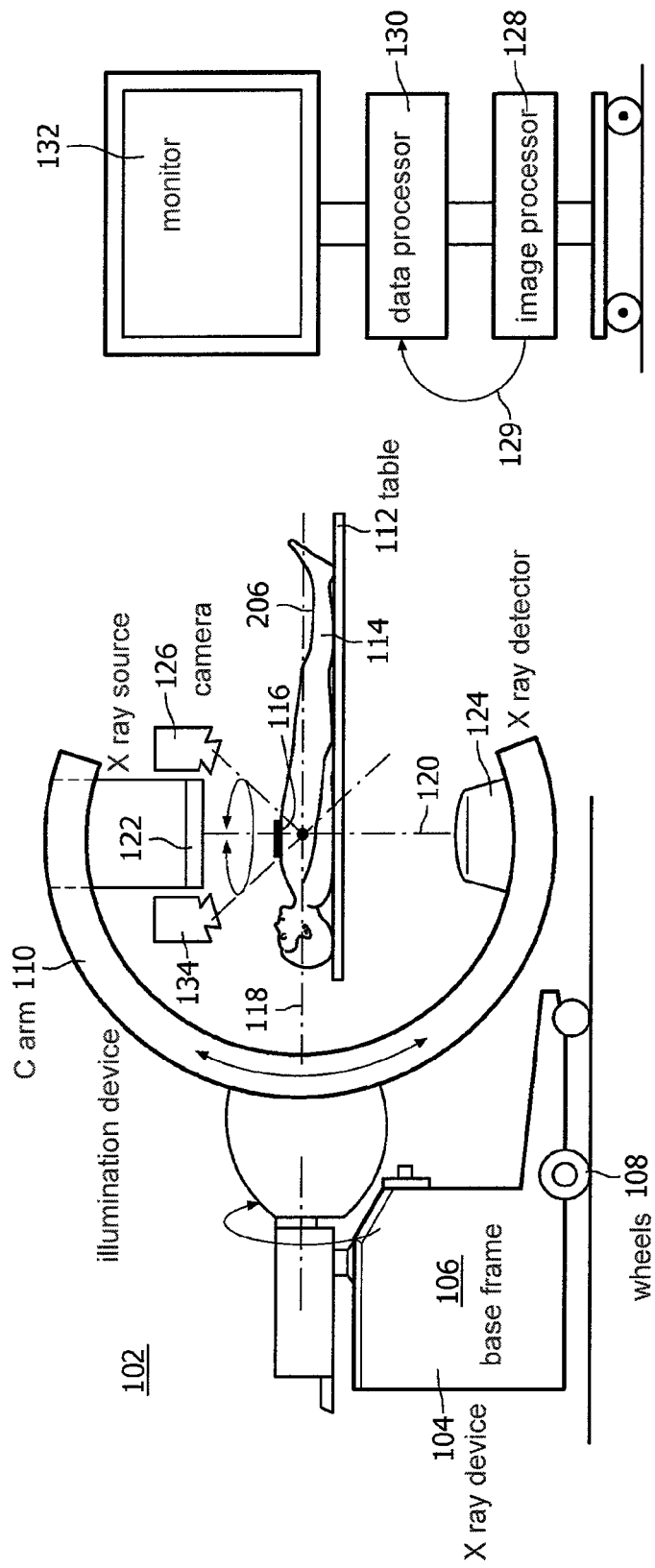
FIG. 1 schematically displays a first embodiment of the system according to the invention comprising an X ray device to which a camera is mounted.
Figure 2:
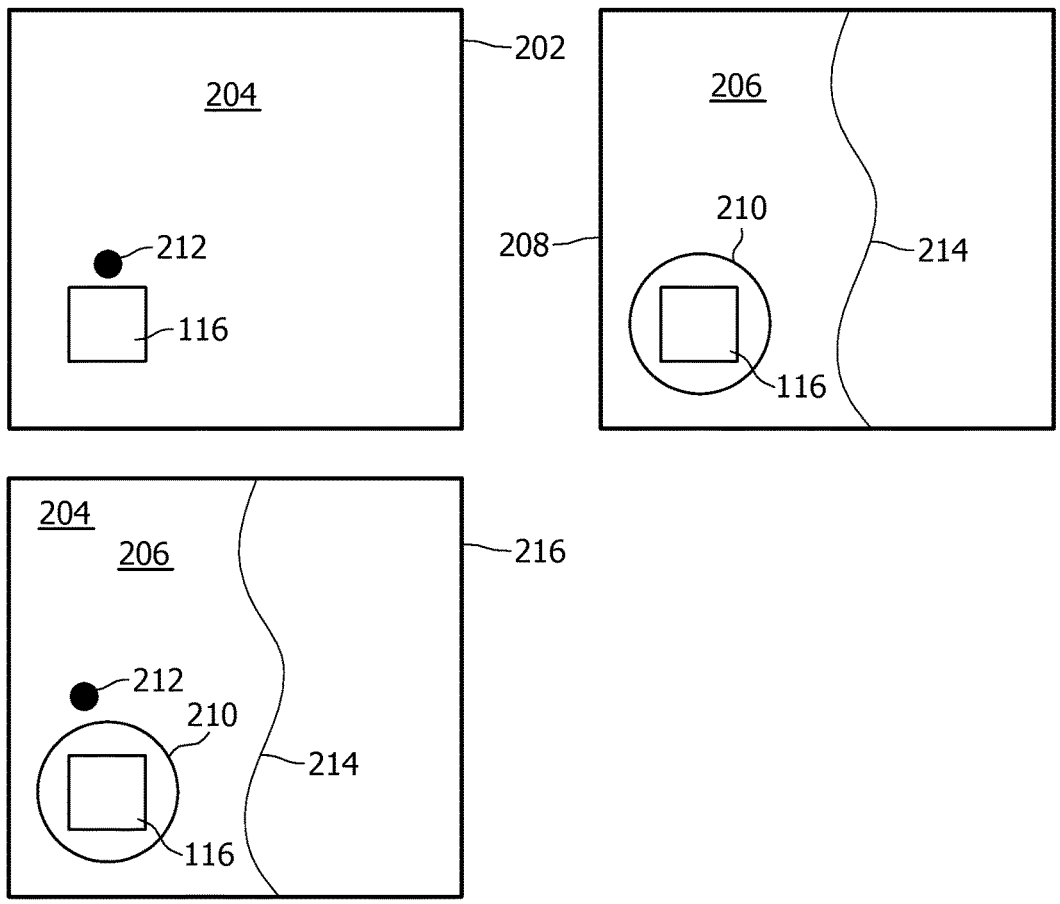
FIG. 2 schematically displays an X ray image, a stream of camera images and a stream of composite images as generated by the embodiment displayed in FIG. 1.

FIG. 1 schematically displays a system 102 comprising an X ray device 104 for providing an X ray image 202 of a patient's interior 204, as displayed in FIG. 2. The X ray device 104, see FIG. 1, has a base frame 106 supported by wheels 108, a movable C arm 110 and a surgical table 112 for supporting a patient 114, which patient 114 is a human being in this particular example. In operational conditions, a fiducial element 116 is mounted on a patient's exterior 206, as depicted in FIG. 2. The movable C arm 110 is rotatable with regard to an axis 118, which axis 118 has a direction corresponding to a main orientation of the surgical table 112, and with regard to an axis 120, which axis 120 is perpendicular to the axis 118 and perpendicular to the surgical table 112. An X ray source 122 and an X ray detector 124, which is preferably a rectangular and flat detector, are mounted on the C arm 110 such that the X ray source and the X ray detector reside opposite one another with respect to the axis 118. A camera 126 for providing a stream of camera images 208 of the patient's exterior 206, as displayed in FIG. 2, is mounted on the C arm 110 aside the X ray source 122. In that way, a predetermined spatial relationship between the X ray image 202 and the stream of camera images 208 is established. In this specific example, the camera 126 is sensitive to electromagnetic radiation having wavelengths in the visible spectrum. An image processor 128 generates an output signal indicative for a movement of the fiducial element 116 based on consecutive camera images.

Referring to FIG. 2, the fiducial element 116 is installed on the patient's exterior 206 at a part 210 of the patient's exterior 206, for making a global movement of the patient's exterior 206 perceptible by at least the camera 126. The fiducial element 116 is detectable in both the X ray image 202 and the stream of camera images 208. In this example, the X ray image 202 furthermore displays a tumor 212 present in the interior 204 of the patient 114. The stream of camera images 208 additionally displays a body contour 214 of the patient 114. Through spatially correlating the fiducial element 116 in the X ray image 202 with said fiducial element 116 in the stream of camera images 208, the X ray image 202 and the stream of camera images 208 allow for spatially correlating.

Referring to FIG. 1, a further data processor 130 renders, during operation, the X ray image 202 and the stream of camera images 208 into a stream of composite images 216 based on the spatial correlating provided by the fiducial element 116. Based on the output signal 129 generated by the image processor 128, the X ray image 202 and hence the stream of composite images 216 is updated regarding a global movement of the fiducial element 116. The stream of composite images 216 display the patient's interior 204 and the patient's exterior 206 in a geometrically overlapping sense, and furthermore the fiducial element 116, the part 210 of the patient's exterior 206, the tumor 212 and the patient's body contour 214.

The camera 126 is configured for providing a beam of electromagnetic radiation for excitation of a contrast agent supplied to the patient 114 in order to provide the stream of camera images 204 and consequently the stream of composite images 216 with a fluorescence characteristic. A monitor 132, as depicted in FIG. 1, displays the stream of composite images 216 to a medical professional (not shown). The system 102 furthermore comprises an illumination device 134 mounted on the C arm 110 aside the X ray source 122, hence aside to the camera 126, for establishing a spatial relationship between the X ray device 104 and the illumination device 126. The illumination device 134 is configured for projecting information comprised in the X ray image 202, for example the tumor 214, on the patient's exterior 206. The illumination device 134 is further arranged for radiation sterilization of e.g. the surgical table 112 and its environment, by way of transmitting a beam of electromagnetic radiation having a wavelength at which the electromagnetic radiation is absorbable by the DNA of infectious agents. In this particular example, a wavelength of about 250 [nm] is employed. The sterilization of the surgical table 112 is performed in between interventions performed at the system 102, preferably by making a full rotation with the rotatable C arm 110.

Figure 3:
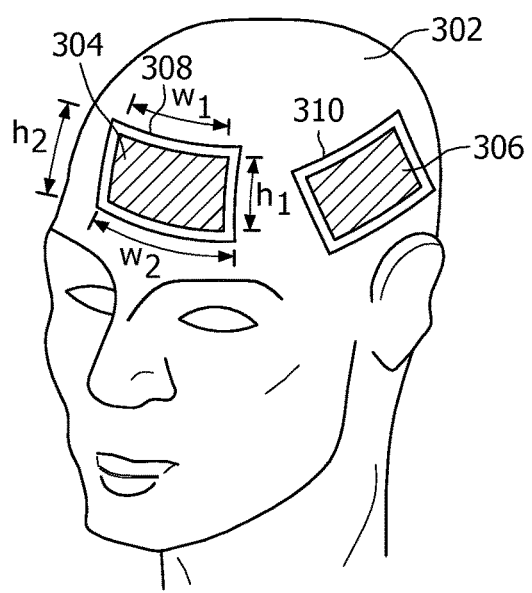
FIG. 3 schematically displays a head of a patient, which patient is provided with a plurality of fiducial elements, wherein fiducial elements have been installed in mutually substantially non-parallel planes.

FIG. 3 schematically depicts a patient's head 302. A plurality of fiducial elements 304 and 306 is installed in mutually non-parallel planes at a patient's exterior. Namely, the fiducial element 304 is mounted on a patient's forehead, more specifically at a part 308 of the patient's exterior whereas the fiducial element 306 is mounted on a side of the patient's head, more specifically at a further part 310 of the patient's exterior. In other cases, one fiducial element or more than two fiducial elements may be installed. The fiducial element 304 and the part 308 of the patient's exterior are provided with substantially equal outer in-plane dimensions. Namely, a width $w_1$ of the fiducial element 304 nearly equals a width $w_2$ of the part 308 of the patient's exterior. Further, a height $h_1$ of the fiducial element 304 nearly equals a height $h_2$ of the part 308 of the patient's exterior. Likewise, the fiducial element 306 and the part 310 of the patient's exterior are provided with substantially equal outer in-plane dimensions. In this particular example, the fiducial elements 304 and 306 are provided with additional layers having a thickness of 100 µm.

Figure 4:
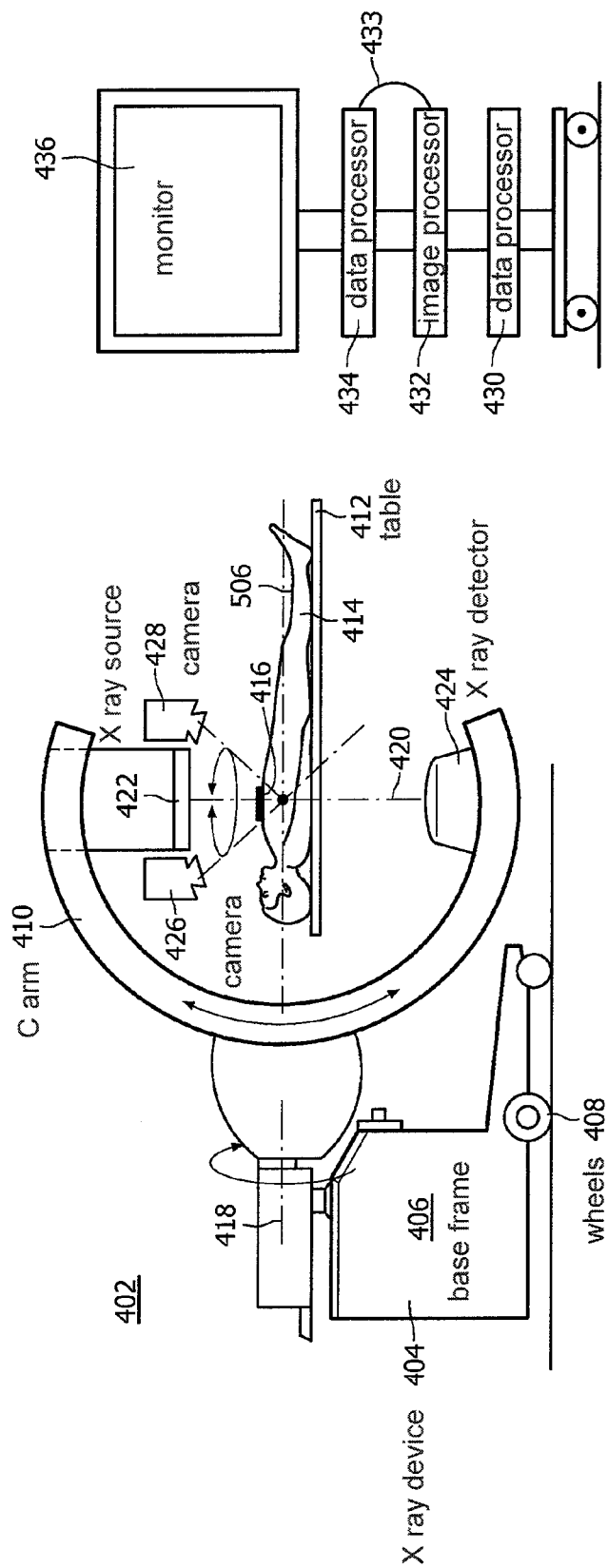
FIG. 4 schematically displays a second embodiment of the system according to the invention comprising an X ray device to which a camera and a further camera are being mounted.
Figure 5:
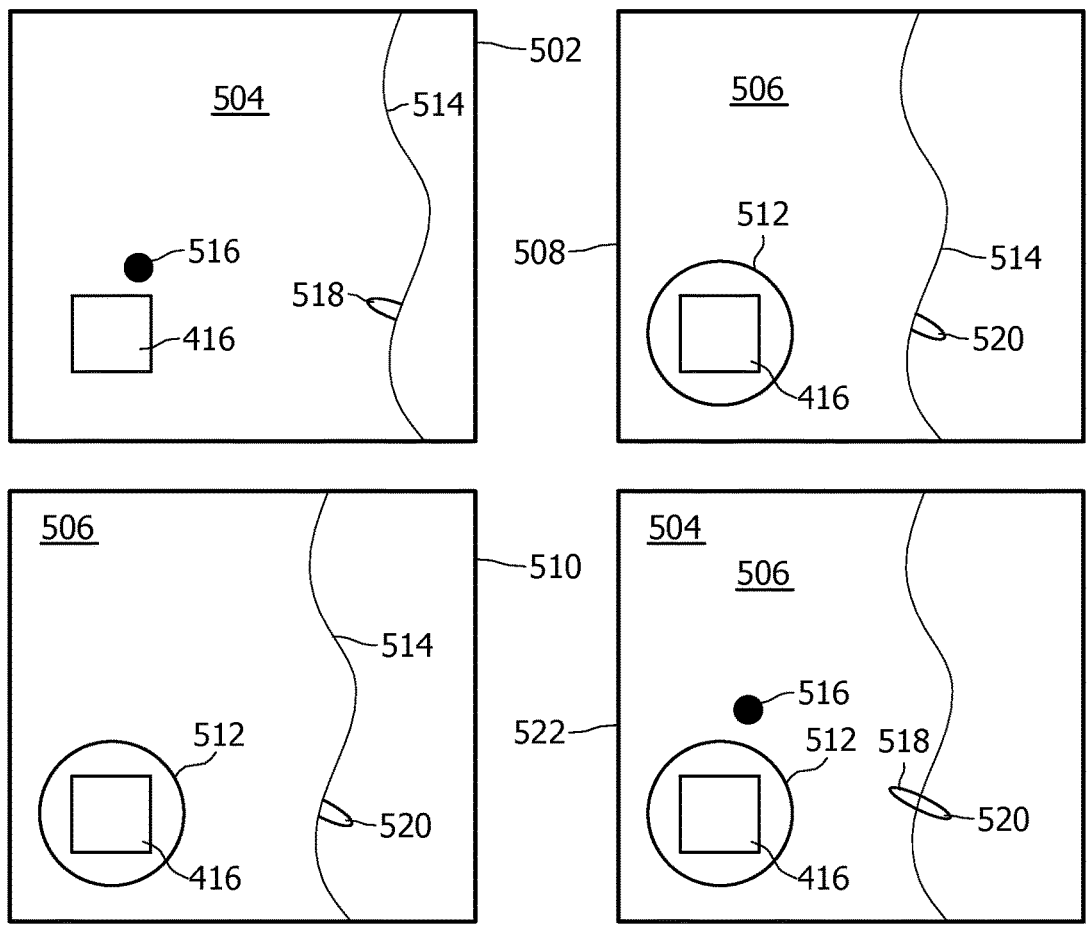
FIG. 5 schematically displays an X ray image, a stream of camera images, a stream of further camera images and a stream of composite images as generated by the embodiment displayed in FIG. 4.

FIG. 4 schematically displays a system 402 comprising an X ray device 404 for providing an X ray image 502 of a patient's interior 504, as displayed in FIG. 5. The X ray device 404, see FIG. 4, has a base frame 406 supported by wheels 408, a movable C arm 410 and a surgical table 412 for supporting a patient 414. In this particular example, the patient 414 is a human being. In operational conditions, a fiducial element 416 is mounted on a patient's exterior 506, as depicted in FIG. 5. Referring to FIG. 4, the C arm 410 is rotatable with regard to the axis 418, which axis 418 has a direction corresponding to a main orientation of the surgical table 412, and with regard to an axis 420, which axis 420 is perpendicular to the axis 418 and perpendicular to the surgical table 412. An X ray source 422 and an X ray detector 424, which is preferably a rectangular and flat detector, are mounted on the C arm 410 such that the X ray source and the X ray detector reside opposite one another with respect to the axis 418. A camera 426, i.e. a first camera, for providing a stream of camera images 508, i.e. a stream of first camera images, of a patient's exterior 506, as depicted in FIG. 5, is mounted on the C arm 410 aside the X ray source 422. A further camera 428, i.e. a second camera, for providing a stream of further camera images 510, i.e. a stream of second camera images, of the patient's exterior 506, as displayed in FIG. 5 is additionally mounted on the C arm 410 aside the X ray source 422. In that way, a predetermined spatial relationship between the X ray image 502 and both the stream of first camera images 508 and the stream of second camera images 510 is established. In addition to that, a mutual predetermined spatial relationship between the stream of first camera images 508 and the stream of second camera images 510 is established. The first camera 426 is responsive to electromagnetic radiation having a first range of wavelength while the second camera 428 is responsive to electromagnetic radiation having a second range of wavelengths. In this specific example, both the first and the second ranges of wavelengths are in the visible part of the electromagnetic spectrum. The first camera 426 and the second camera 428 are mounted at different positions on the C arm 410. Thereby a parallax is introduced between optical axes associated with the first and second camera 426 and 428.

Referring to FIG. 5, the fiducial element 416 is installed on the patient's exterior 506 at the part 512 of the patient's exterior 506, for making a global movement of the patient's exterior 506 perceptible by the first camera 426 and the second camera 428. The fiducial element 416 is detectable in the X ray image 502, the stream of first camera images 508 and the stream of second camera images 510. Through spatially correlating the fiducial element 416 in the X ray image 502 with said fiducial element 416 in the stream of first camera images 508 and the stream of second camera images 510, the X ray image 502, the stream of first camera images 508 and the stream of second camera images 510 allow for spatially correlating. In this particular example, the X ray image 502 displays the patient's interior 504, a part 512 of the patient's exterior 506, a contour 514 of the patient's exterior 506, a tumor 516 or another medical deficiency present in the interior 504 of the patient 414, and a medical instrument 518, which medical instrument 518 is partly present in the patient's interior 504 in this particular example. For the purpose of displaying the contour 514, an amount of X ray radiation provided by the X ray source 422 to the patient 414 must be sufficiently large, i.e. the amount of X ray radiation is to enable a detectability of a patient's soft tissue in the X ray image 502. Both the stream of first camera images 508 and the stream of second camera images 510 display the patient's exterior 506, the part 512 of the patient's exterior 506, the contour 514 of the patient's exterior 506, and a part 520 of the medical instrument 518, which part 520 is not present in the patient's interior 504.

Referring to FIG. 4, a data processor 430 renders the stream of first camera images 508 and the stream of second camera images 510 into a stream of composite camera images (not shown). Based on the parallax between the optical axes of the first and second cameras 426 and 428, the stream of composite camera images allows for displaying three dimensional characteristics. An image processor 432 generates an output signal 433 indicative for a movement of the fiducial element 416 based on consecutive images comprised in the stream of composite camera images. A further data processor 434 renders the X ray image 502 and the stream of composite camera images into a stream of composite images 522 based on the spatial correlating provided by the fiducial element 416. A monitor 436 displays the stream of composite images 522 to a medical professional.

Referring to FIG. 5, the stream of composite images 522 displays the patient's interior 504 and the patient's exterior 506 in a geometrically overlapping sense, and furthermore the part 512 of the patient's exterior 506, the contour 514 of the patient's exterior 506, the tumor 516 and the medical instrument 518. Based on the output signal 433 generated by the image processor 432, the X ray image 502, and hence the stream of composite images 522, is updated regarding a global movement of the fiducial element 416.

While the invention has been illustrated and described in detail in the drawings and in the foregoing description, the illustrations and the description are to be considered illustrative or exemplary and not restrictive. It is noted that the system according to the invention and all its components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features defined in the set of claims are part of the invention.

The invention claimed is:

1. A system for detecting a patient's global movement during imaging procedures, the system comprising:
  at least one camera configured to provide a stream of images of a part of a patient's exterior and body contour;
  a fiducial element having a metal layer with a thickness small enough to be conformable to said part of the patient's exterior and an adhesive layer configured to be attached to the part of a patient's exterior, the fiducial element including the metal layer being configured to conform to said part of the patient's exterior when attached by the adhesive to said part of the patient's exterior to follow a part contour of said part of the patient's exterior, wherein the fiducial element is detectable in the stream of images, wherein the fiducial element has an in-plane stiffness larger than an in-plane stiffness of said part of the patient's exterior, and wherein the fiducial element and said part of the patient's exterior are provided with equal outer in-plane dimensions;
  an image processor configured to detect a displacement of the fiducial element based on consecutive images comprised in the stream of images, and configured to generate an output signal indicative of said displacement; and
  a device configured to generate and render an X ray image of said part of a patient's interior,
  wherein the in-plane stiffness and the outer in-plane dimensions of the fiducial element are such that local movements of said part of the patient's exterior relative to a skeleton of the patient along a direction parallel to a plane of the fiducial element are reduced, and
  wherein a ratio of the in-plane stiffness of the fiducial element to the in-plane stiffness of said part of the patient's exterior is large enough to reduce the local movements while allowing the fiducial element to conform to said part of the patient's exterior when attached by the adhesive.

2. The system according to claim 1, wherein the fiducial element has a buckling stiffness which is larger than a buckling stiffness of said part of the patient's exterior.

3. The system according to claim 1, further comprising a further fiducial element, wherein the fiducial element and the further fiducial element are installed in mutually non-parallel planes.

4. The system according to claim 1, wherein the at least one camera comprises a first camera and a second camera, and wherein the first camera and the second camera are mutually rigidly supported for establishing a mutually predetermined spatial relationship, and the system further comprising a data processor configured to render the stream of images into a stream of composite images based on a spatial correlation between the stream of images provided by the first camera and the second camera, and wherein the spatial correlation is established by the fiducial element.

5. The system according to claim 1, further comprising a data processor, wherein the at least one camera is supported by the device for establishing a predetermined spatial relationship between the stream of images and the X ray image, and wherein the fiducial element is detectable in the X ray image, and wherein the data processor is configured to update the X ray image based on the output signal generated by the image processor, and based on a spatial correlation between the stream of images and the X ray image, wherein the spatial correlation is established by the fiducial element, wherein the device includes an X ray source configured to provide an amount of X ray radiation that enables detectability of soft tissue including the body contour in the X ray image.

6. The system according to claim 5, wherein the data processor is further configured to render the X ray image and the stream of images into a stream of composite images based on said spatial correlation between the stream of images and the X ray image.

7. The system according to claim 5, wherein the device comprises a movable geometry, and wherein the at least one camera is supported by said movable geometry.

8. The system according to claim 5, further comprising an instrument configured to perform a medical intervention, wherein the instrument is detectable in the stream of images and in the X ray image, and wherein the data processor is further configured to determine a location and orientation of the instrument in the patient's interior based on the spatial correlation between the stream of images and the X ray image.

9. The system of claim 8, wherein the instrument comprises pulsed light emitting diodes for enhancing detectability of the instrument in the stream of images provide by the at least one camera.

10. The system according to claim 5, further comprising an illumination device configured to project information comprised in the X ray image onto said part of the patient's exterior based on the spatial correlation between the stream of images and the X ray image, wherein the data processor is further configured to compensate the projection of the information comprised in the X ray for curvature of the patient's exterior based on the stream of camera images.

11. The system according to claim 10, wherein the illumination device is supported by the device for establishing a further predetermined spatial relationship between the illumination device and the device.

12. The system according to claim 10, wherein the illumination device is configured to provide radiation sterilization.

13. The system according to claim 1, wherein the at least one camera is configured to provide a beam of electromagnetic radiation for excitation of a contrast agent supplied to the patient.

14. The system of claim 1, wherein the outer in-plane dimension of the fiducial element exceeds 10 cm by 10 cm to reduce movement of the patient's exterior along the direction parallel to the plane of the fiducial element.

15. The system of claim 1, wherein the in-plane stiffness of the fiducial element is stiffness along the direction parallel to the plane of the fiducial element and is different from a stiffness of the fiducial element along a direction perpendicular to the plane of the fiducial element.

16. A system for detecting a patient's global movement during imaging procedures, the system comprising:

at least one camera configured to provide a stream of images of a part of a patient's exterior and body contour;

a fiducial element having an adhesive layer configured to be attached to the part of a patient's exterior, the fiducial element being configured to conform to said part of the patient's exterior when attached by the adhesive to said part of the patient's exterior to follow a part contour of said part of the patient's exterior, wherein the fiducial element is detectable in the stream of images, wherein the fiducial element has an in-plane stiffness larger than an in-plane stiffness of said part of the patient's exterior, and wherein the fiducial element and said part of the patient's exterior are provided with equal outer in-plane dimensions;

an image processor configured to detect a displacement of the fiducial element based on consecutive images comprised in the stream of images, and configured to generate an output signal indicative of said displacement; and a device configured to generate and render an X ray image of said part of a patient's interior, wherein the in-plane stiffness and the outer in-plane dimensions of the fiducial element are such that local movements of said part of the patient's exterior relative to a skeleton of the patient along a direction parallel to a plane of the fiducial element are prevented, wherein the outer in-plane dimension of the fiducial element exceeds 1 cm by 1 cm, and wherein the ratio of the in-plane stiffness of the fiducial element to the in-plane stiffness of said part of the patient's exterior is 100 to 1 to reduce movement of the patient's exterior along the direction parallel to the plane of the fiducial element.

17. A system for detecting a patient's global movement during imaging procedures, the system comprising:

at least one camera configured to provide a stream of images of a part of a patient's exterior;

at least one fiducial element mountable on the part of the patient's exterior, wherein the fiducial element is detectable in the stream of images, wherein the fiducial element has an in-plane stiffness larger than an in-plane stiffness of said part of the patient's exterior, and wherein the fiducial element and the part of the patient's exterior are provided with equal outer in-plane dimensions; and an image processor configured to detect a displacement of the fiducial element based on consecutive images comprised in the stream of images, and configured to generate an output signal indicative of said displacement, wherein a ratio of the in-plane stiffness of the fiducial element to the in-plane stiffness of said part of the patient's exterior exceeds 10 to 1, and wherein the outer in-plane dimension of the fiducial element exceeds 10 cm by 10 cm to reduce movement of the patient's exterior along the direction parallel to the plane of the fiducial element.

\* \* \* \* \*